US00PP08176P

United States Patent [19]

Saville

[11] Patent Number: Plant 8,176

[45] Date of Patent: Mar. 16, 1993

[54] MINIATURE ROSE PLANT NAMES SAVAWHOOP

[75] Inventor: F. Harmon Saville, Rowley, Mass.

[73] Assignee: Nor'East Miniature Roses, Inc., Rowley, Mass.

[21] Appl. No.: 740,506

[22] Filed: Aug. 5, 1991

[51] Int. Cl.[5] ..... A01H 5/00

[52] U.S. Cl. ..... Plt./7.1

[58] Field of Search ..... Plt./7.1, 2

[56] References Cited

U.S. PATENT DOCUMENTS

P.P. 7,588 7/1991 Carruth ..... Plt. 7.1

*Primary Examiner*—Howard J. Locker

*Attorney, Agent, or Firm*—Christie, Parker & Hale

[57] ABSTRACT

A new miniature rose with red and white bicolor flowers of good form.

1 Drawing Sheet

SUMMARY OF THE INVENTION

The present invention relates to a new and distinct variety of rose plant of the miniature rose class, which was created by me by crossing as seed parent an unnamed, unpatented seedling of my creation and as pollen parent the rose known as "Party Girl" (U.S. Plant Pat. No. 4,598). The varietal denomination of this new rose is "Savawhoop".

Among the novel characteristics possessed by this new variety which distinguishes it from its parent and all other varieties of which I am aware is its unusual red and white bicolor flowers of good form.

Asexual reproduction by propagation by cuttings of the new variety as performed in Essex County, Mass., shows that the foregoing and other distinguishing characteristics come true to form and are established and transmitted through succeeding propagations.

BRIEF DESCRIPTION OF ILLUSTRATION

The accompanying illustration shows typical specimens of the flowers of the new variety in different stages of development depicted in color as nearly true as it is reasonably possible to make the same in a color illustration of this character.

DETAILED DESCRIPTION OF THE NEW VARIETY

The following is a detailed description of my new variety, with color terminology in accordance with The Royal Horticultural Society Color Chart (R.H.S.C.C.). The terminology used in color description herein refers to plate numbers in the aforementioned color chart.

Parentage:

*Seed parent.*—Unnamed seedling.

*Pollen parent.*—"Party Girl".

Class: Miniature.

The following observations are made of specimens grown outdoors in Essex County, Mass., during the month of July.

FLOWER

Blooming habit: Continuous, recurrent.

A. Bud:

(1) *Size.*—Medium.

(2) *Form.*—Ovoid, pointed.

(3) *Color.*—As sepals divide, bud color is near 155A-D with near 51A to 52A at petal edge, washing into outer white portion of petal undersurface.

(4) *Sepals.*—Relatively smooth, longer than bud.

(5) *Peduncle.*—Length — about $\frac{3}{4}$ inches. Aspect — straight. Strength — erect. Color — near 144C.

B. Bloom:

(1) *Size.*—Average size when fully expanded — about $1\frac{3}{4}$ inches.

(2) *Borne.*—Singly, one to a stem and several together in sprays of 3 to 10 blooms.

(3) *Form.*—High centered at first; outer petals remaining at first loosely rolled under and some quill to points; outer petals tend to have pointed apices.

(4) *Petalage.*—Number of petals under normal conditions —about 28 to 32.

(5) *Color.*—After sepals fall and petals unfurl, predominant flower color of visible petal undersurface is near 155A-D flushed with red and near 51A-D and 53C to 53D to 54A-B at and near petal edges. Red coloration washes and suffuses into white at outer portion of petals with hazy but perceptible demarcation. Flowers retain the bicoloration of near white with red edging as they open with red coloring bleeding through petal top to petal undersurface at petal margins. Petal top surface displays bicoloration ranging from near 53C-D to 54A-B on inner petals as flowers open and mature. Deepest tonality, 53B-D is at petal edges in $\frac{1}{3}$ to $\frac{1}{2}$ open blooms, through 51A-52A to 52C-D as red washes or suffuses into white areas of petals. Deep red hues may be seen where petals bunch but red coloration remains at petal edges. Consistent bicoloring remains after three or more days with little lightening of the red coloration. General tonality from a distance is a red and white bicolor. Color at point of petal attachment is near 155A. Open bloom displays attractive slightly lighter red and white coloration.

Petals:

(1) *Texture.*—Thick.

(2) *Appearance.*—Inside velvety and outside satiny.

(3) *Form.*—Very wide fan shaped; some pointed apices.

(4) *Arrangement.*—Regularly arranged, imbricated.
(5) *Petaloids in center.*—Few.
(6) *Persistence.*—Average.
(7) *Fragrance.*—Slight.
(8) *Lasting quality.*—Long lasting quality on plant and after cutting.

REPRODUCTIVE ORGANS

A. Stamens, filaments and anthers:
*Arrangement.*—Regularly arranged around styles.
*Color.*—Near 24A.
B. Pollen:
*Color.*—Near 24A.
C. Styles: Thin, medium length.
D. Stigmas:
*Color.*—near 154D.
E. Hips: None observed.

PLANT

A. Form: Compact.
B. Growth: Very vigorous, uniform branching.
*Height attained.*—About 15 to 18 inches.
C. Foliage: Compound 5 to 7 leaflets.
(1) *Size.*—Medium.
(2) *Quantity.*—Abundant.
(3) *Color.*—New foliage: Upper side — near 137A flushed with near 187C. Underside — near 137C flushed with near 187C. Old foliage: Upper side — near 136A. Underside —0 near 137D.
(4) *Shape.*—Oval, pointed.

(5) *Texture.13* Upper side is semi-glossy; underside is matte.
(6) *Edge.*—Serrate.
(7) *Serration.*—Regular.
(8) *Leaf stem.*—Color — near 137C. Under side — 146D.
(9) *Stipules.*—Medium length, not bearded.
(10) *Resistance to Disease.*—Blackspot — Average. Mildew — Average. Rust — Average.
D. Wood:
(1) *New wood.*—Color — near 146A. Bark — smooth.
(2) *Old wood.*—Color — near 146B. Bark — smooth.
E. Thorns:
*Quantity (main stalk).*—ordinary.
*On laterals from stalk.*—few.
*Form.*—Long, thin, slanted slightly downward.
*Length.*—Medium.
*Color.*—Near 199D.
*Position.*—Irregular.
*Prickles.*—None.
F. Winter hardiness: Needs protection in severe climates.

I claim:

1. A new and distinct variety of rose plant of the miniature rose class, substantially as shown and described.

* * * * *

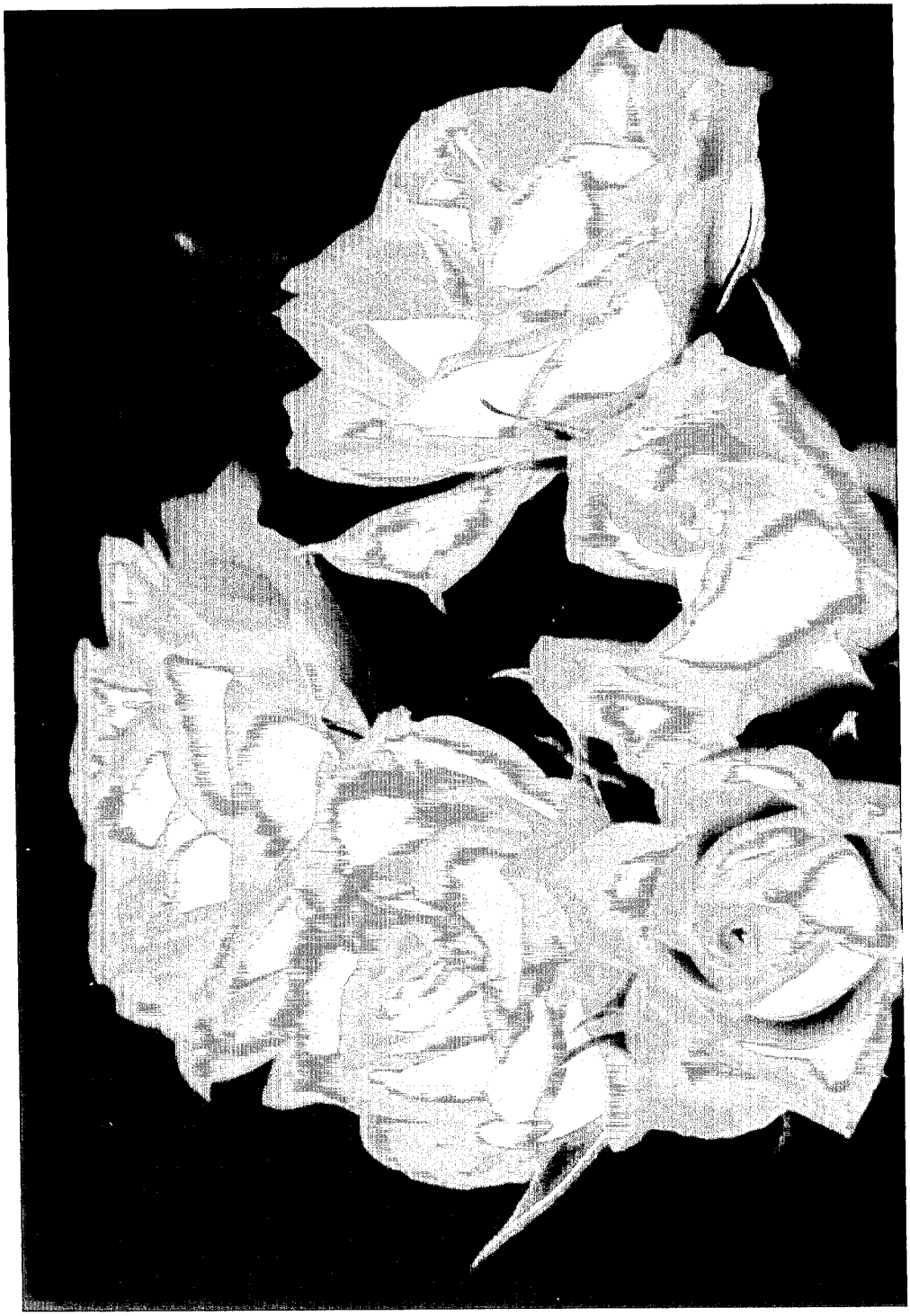

UNITED STATES PATENT AND TRADEMARK OFFICE

CERTIFICATE OF CORRECTION

PATENT NO. : Plant 8,176

DATED : March 16, 1993

INVENTOR(S) : F. Harmon Saville

It is certified that error appears in the above-identified patent and that said Letters Patent is hereby corrected as shown below:

On title page, item

[54] Title, change "NAMES" to -- NAMED --.

Column 3, line 29, before "near" delete "0".

Column 4, line 1, after "Texture" delete "13" and insert therefor a dash.

Signed and Sealed this

Eighth Day of February, 1994

Bruce Lehman

*Attest:*

BRUCE LEHMAN

*Attesting Officer*

*Commissioner of Patents and Trademarks*